United States Patent
Kowshik et al.

(10) Patent No.: US 12,390,123 B2
(45) Date of Patent: Aug. 19, 2025

(54) SYSTEMS AND METHODS FOR CONFIGURING COMPONENTS IN A MINIMALLY INVASIVE INSTRUMENT

(71) Applicant: INTUITIVE SURGICAL OPERATIONS, INC., Sunnyvale, CA (US)

(72) Inventors: Anoop B. Kowshik, Saratoga, CA (US); Caitlin Q. Donhowe, Mountain View, CA (US); Vincent Duindam, San Francisco, CA (US); Carolyn M Fenech, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 373 days.

(21) Appl. No.: 17/894,515

(22) Filed: Aug. 24, 2022

(65) Prior Publication Data

US 2022/0400975 A1    Dec. 22, 2022

Related U.S. Application Data

(63) Continuation of application No. 16/752,064, filed on Jan. 24, 2020, now Pat. No. 11,471,066, which is a
(Continued)

(51) Int. Cl.
*A61B 5/06* (2006.01)
*A61B 34/20* (2016.01)
(Continued)

(52) U.S. Cl.
CPC .............. *A61B 5/06* (2013.01); *A61B 5/065* (2013.01); *A61B 34/20* (2016.02);
(Continued)

(58) Field of Classification Search
CPC ... A61B 5/06; A61B 5/065; A61B 2034/2051; A61B 2034/2061; A61B 2034/301; A61B 2090/3614
See application file for complete search history.

(56) References Cited

U.S. PATENT DOCUMENTS 5,797,869 A    8/1998    Martin et al.
6,380,732 B1   4/2002    Gilboa
(Continued)

FOREIGN PATENT DOCUMENTS

JP    2005052646 A    3/2005
JP    2007507294 A    3/2007
(Continued)

OTHER PUBLICATIONS

Co-pending U.S. Appl. No. 61/658,305, filed Jun. 11, 2012 (ISRG04560/PROV/US).
(Continued)

*Primary Examiner* — Joel F Brutus
(74) *Attorney, Agent, or Firm* — Haynes & Boone, LLP.

(57) ABSTRACT

A catheter system comprises an elongate flexible catheter and a support structure mounted on the catheter. The support structure comprises a first alignment feature and a second alignment feature. The first alignment feature is configured to mate with a first sensor component and the second alignment feature configured to mate with a second sensor component. When the system further comprises a first sensor component mated with the first alignment feature and a second sensor component mated with the second alignment feature, the first sensor component is fixed relative to the second sensor component in at least one degree of freedom at the support structure by the first and second alignment features.

20 Claims, 7 Drawing Sheets

Related U.S. Application Data continuation of application No. 16/028,062, filed on Jul. 5, 2018, now Pat. No. 10,568,539, which is a continuation of application No. 15/627,099, filed on Jun. 19, 2017, now Pat. No. 10,022,067, which is a continuation of application No. 13/964,724, filed on Aug. 12, 2013, now Pat. No. 9,730,611.

(60) Provisional application No. 61/682,976, filed on Aug. 14, 2012.

(51) Int. Cl.
    *A61B 34/30* (2016.01)
    *A61B 90/00* (2016.01)
    *A61M 25/01* (2006.01)

(52) U.S. Cl.
    CPC ............... *A61B 2034/2051* (2016.02); *A61B 2034/2061* (2016.02); *A61B 34/30* (2016.02); *A61B 2034/301* (2016.02); *A61B 2090/3614* (2016.02); *A61M 25/0147* (2013.01); *A61M 2025/0166* (2013.01)

(56) References Cited

U.S. PATENT DOCUMENTS

| | | | |
|---|---|---|---|
| 6,389,187 B1 | 5/2002 | Greenaway et al. |
| 7,048,716 B1 | 5/2006 | Kucharczyk et al. |
| 7,772,541 B2 | 8/2010 | Froggatt et al. |
| 7,930,065 B2 | 4/2011 | Larkin et al. |
| 7,942,868 B2 | 5/2011 | Cooper et al. |
| 7,998,112 B2 | 8/2011 | Chow et al. |
| 8,016,749 B2 | 9/2011 | Clerc et al. |
| 8,155,728 B2 | 4/2012 | Voegele et al. |
| 9,730,611 B2 | 8/2017 | Kowshik et al. |
| 10,022,067 B2 | 7/2018 | Kowshik et al. |
| 10,568,539 B2 | 2/2020 | Kowshik et al. |
| 2006/0013523 A1 | 1/2006 | Childlers et al. |
| 2006/0149134 A1 | 7/2006 | Soper et al. |
| 2009/0137952 A1 | 5/2009 | Ramamurthy et al. |
| 2009/0324161 A1 | 12/2009 | Prisco |
| 2010/0082041 A1 | 4/2010 | Prisco |
| 2010/0317962 A1* | 12/2010 | Jenkins .................. A61B 18/18 600/411 |
| 2010/0331820 A1 | 12/2010 | Prisco et al. |
| 2011/0077498 A1 | 3/2011 | McDaniel |
| 2011/0119023 A1 | 5/2011 | Duindam et al. |
| 2012/0123395 A1 | 5/2012 | Stoy et al. |
| 2020/0163581 A1 | 5/2020 | Kowshik et al. |

FOREIGN PATENT DOCUMENTS

| | | | |
|---|---|---|---|
| JP | 2011072782 A | 4/2011 |
| WO | WO-2006079108 A1 | 7/2006 |
| WO | WO-2006124390 A2 | 11/2006 |
| WO | WO-2007111737 A2 | 10/2007 |
| WO | WO-2007146987 A2 | 12/2007 |
| WO | WO-2009023801 A1 | 2/2009 |
| WO | WO-2010117625 A2 | 10/2010 |
| WO | WO-2011048509 A1 | 4/2011 |

OTHER PUBLICATIONS

Extended European Search Report for Application No. EP13829392.3, mailed on Mar. 15, 2016, 6 pages (ISRG04550/EP).

International Search Report and Written Opinion for Application No. PCT/US13/54568, mailed on Nov. 14, 2013, 9 pages (ISRG04550/PCT).

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

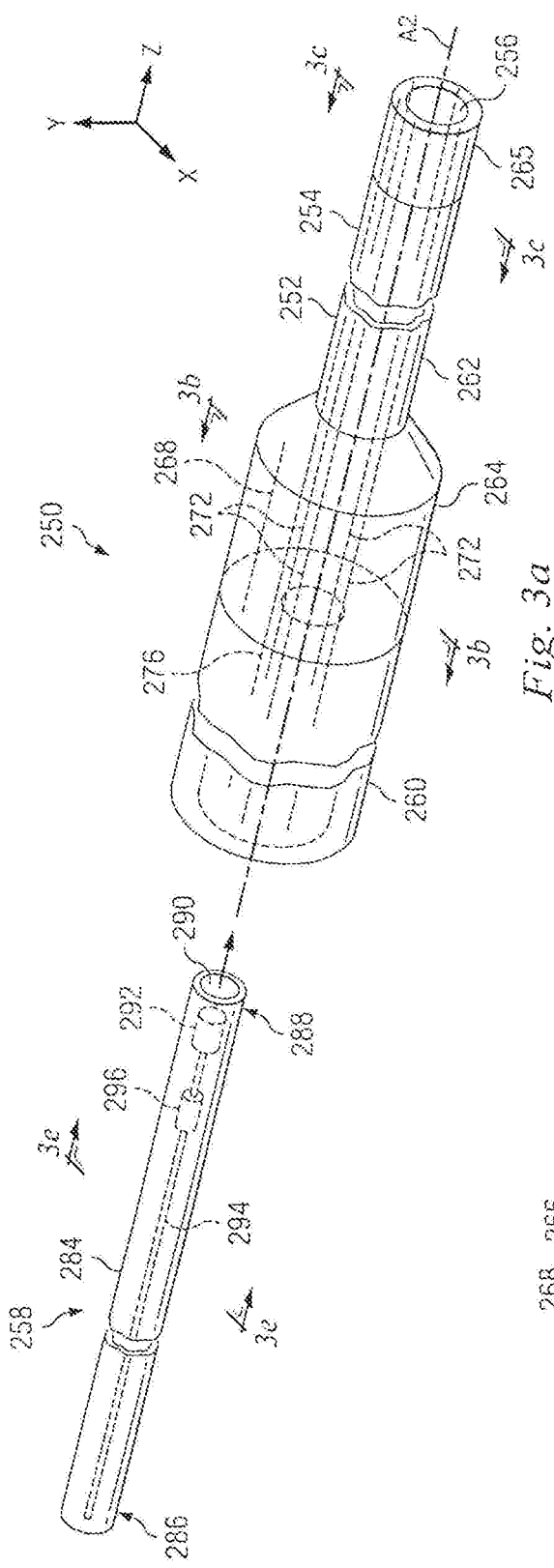
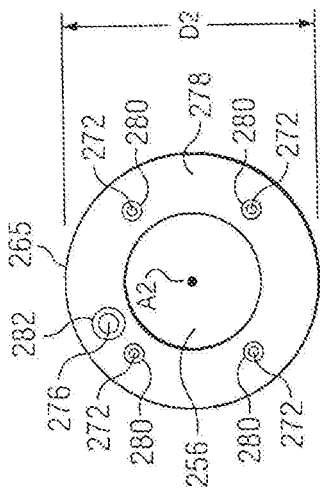
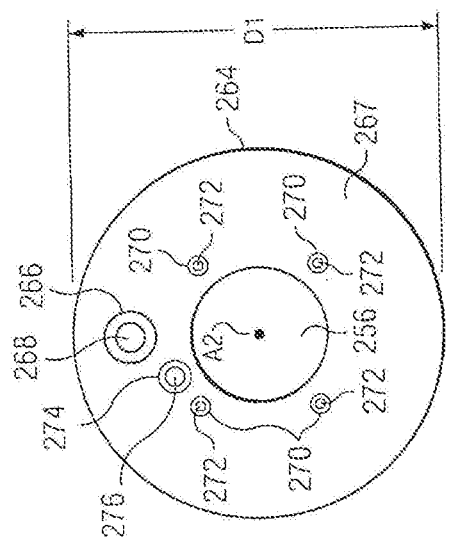

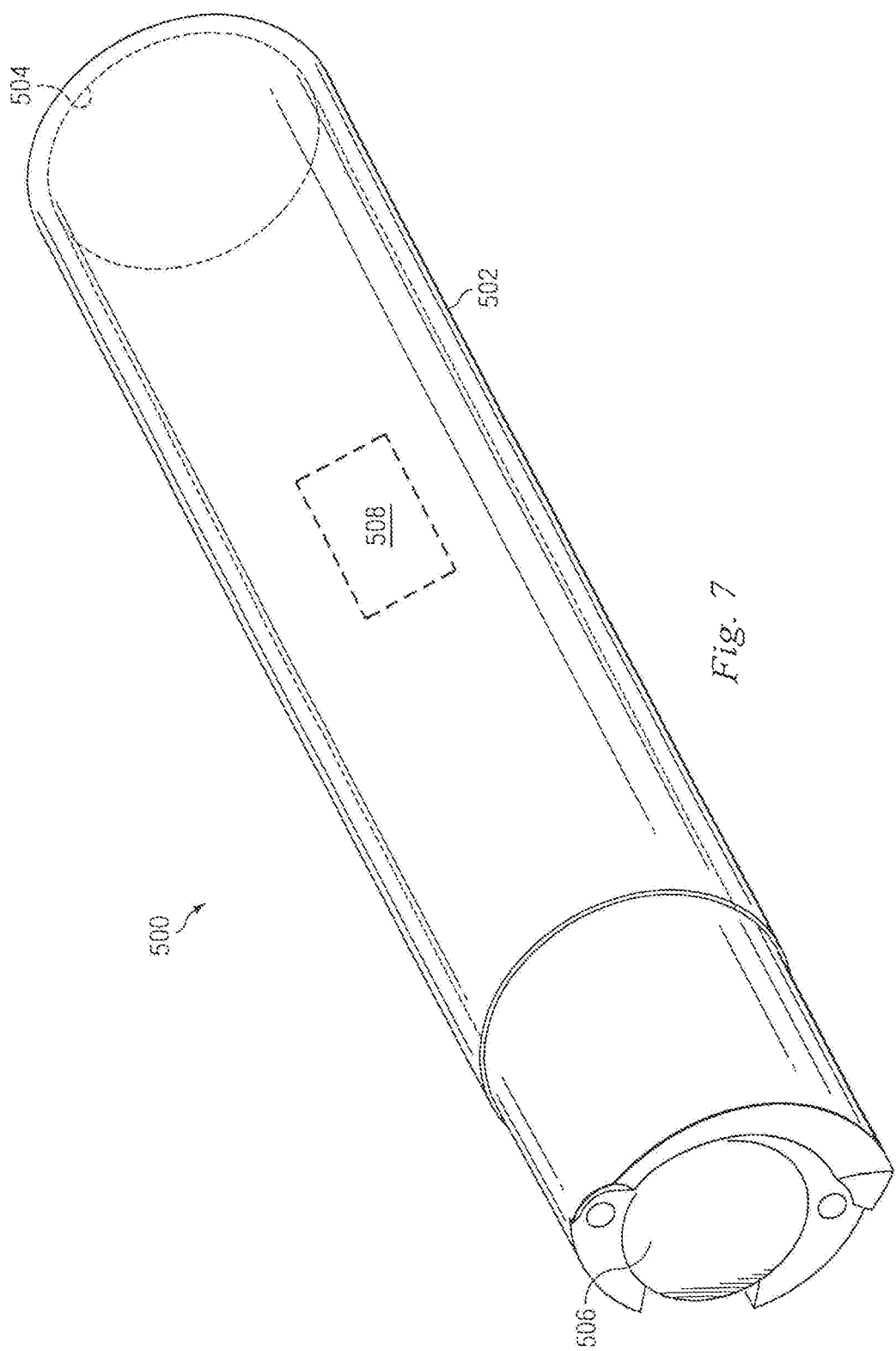

SYSTEMS AND METHODS FOR CONFIGURING COMPONENTS IN A MINIMALLY INVASIVE INSTRUMENT

CROSS-REFERENCE TO RELATED APPLICATIONS

This application is continuation application of U.S. patent application Ser. No. 16/752,064, filed Jan. 24, 2020, which is a continuation application of U.S. patent application Ser. No. 16/028,062, filed Jul. 5, 2018, which is a continuation of U.S. patent application Ser. No. 15/627,099, filed Jun. 19, 2017, which is a continuation of U.S. patent application Ser. No. 13/964,724, filed on Aug. 12, 2013, which claims the benefit of U.S. Provisional Patent Application No. 61/682,976, filed on Aug. 14, 2012, both all of which are incorporated by reference herein in their entirety.

FIELD

The present disclosure is directed to systems and methods for minimally invasive surgery, and more particularly to systems and methods for configuring components in a minimally invasive instrument.

BACKGROUND

Minimally invasive medical techniques are intended to reduce the amount of tissue that is damaged during diagnostic or surgical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert surgical instruments to reach a target tissue location. To reach the target tissue location, the minimally invasive surgical instruments may navigate natural or surgically created connected passageways in anatomical systems, such as the lungs, the colon, the intestines, the kidneys, the heart, the brain, the circulatory system, or the like. Navigational assist systems help the clinician route the surgical instruments and avoid damage to the anatomy. These systems can incorporate the use of sensors to more accurately describe the shape, pose, and location of the surgical instrument in real space or with respect to previously recorded or concurrently gathered images. In a dynamic anatomical system and/or in an anatomical region dense with many anatomical passageways, accurately determining the shape, pose, and location of the surgical instrument may depend, at least in part, upon precision in the relative placement of sensor systems, steering systems, and imaging components. Improved systems and methods are needed for tight control of the relative placement of the systems and components of minimally invasive instruments.

SUMMARY

The embodiments of the invention are summarized by the claims that follow the description.

In one embodiment, a catheter system comprises an elongate flexible catheter and a support structure mounted on the catheter. The support structure comprises a first alignment feature and a second alignment feature. The system further comprises a first sensor component mated with the first alignment feature and a second sensor component mated with the second alignment feature. The first sensor component is fixed relative to the second sensor component in at least one degree of freedom at the support structure by the first alignment feature.

In another embodiment, a catheter system comprises an elongate flexible catheter and a first support structure mounted on the catheter. The first support structure comprises a first alignment feature and a second alignment feature. The system further comprises a second support structure mounted on the catheter. The second support structure comprises a third alignment feature and a fourth alignment feature. The system further comprises a first sensor component comprising a first portion mated with the first alignment feature and a second portion mated with the third alignment feature. The system further comprises a steering wire mated with the second alignment feature and the fourth alignment feature. The first sensor component is fixed relative to the steering wire at the first support structure in at least one degree of freedom by the first alignment feature and the second alignment feature. The first sensor component is fixed relative to the steering wire at the second support structure in at least one degree of freedom by the third alignment feature and the fourth alignment feature.

In another embodiment, a method comprises providing a flexible catheter. The flexible catheter comprises a first sensor component, a second sensor component, and a first support structure. The first support structure comprises a first alignment feature and a second alignment feature. The first sensor component is fixed in a predetermined position relative to the second sensor component at the first support structure. The method further comprises acquiring data from the first sensor component and the second sensor component. The method also comprises determining a pose of at least a portion of the flexible catheter based on the predetermined position and the data from the first sensor component and the second sensor component.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and amity and does not in itself dictate a relationship between the various embodiments and/or configurations discussed.

FIG. 3a is an illustration of an exploded probe assembly according to an embodiment of the present disclosure.

FIG. 3b is a cross-sectional view of an alignment support structure of the catheter of FIG. 3a.

FIG. 3c is a cross-sectional view of another alignment support structure of the catheter of FIG. 3a.

FIG. 3e is a cross-sectional view of the probe of FIG. 3a.

FIG. 7 is a perspective view of a probe according to an embodiment of the disclosure.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention, And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X,Y,Z coordinates). As used herein, the term "orientation" refers to the rotational placement of an object or a portion of an object (three degrees of rotational freedom e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
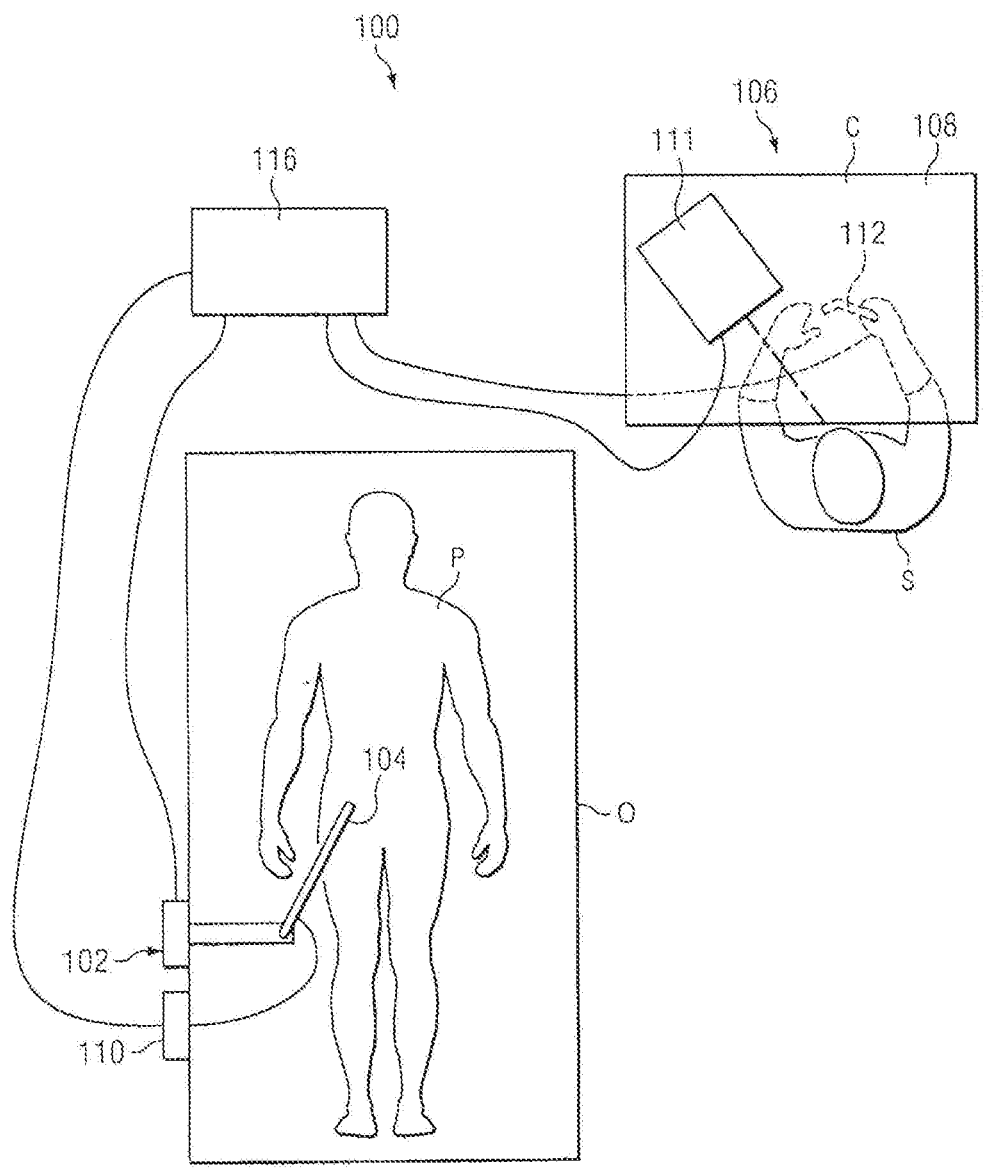
FIG. 1 is a diagrammatic top view of robotic surgical system, in accordance with embodiments of the present disclosure.

Referring to FIG. 1 of the drawings, a robotic surgical system is generally indicated by the reference numeral 100. As shown in FIG. 1, the robotic system 100 generally includes a surgical manipulator assembly 102 for operating a surgical instrument 104 in performing various procedures on the patient P. The assembly 102 is mounted to or near an operating table O. A master assembly 106 allows the surgeon S to view the surgical site and to control the slave manipulator assembly 102.

The master assembly 106 may be located at a surgeon's console C which is usually located in the same room as operating table O. However, it should be understood that the surgeon S can be located in a different room or a completely different building from the patient P. Master assembly 106 generally includes an optional support 108 and one or more control device(s) 112 for controlling the manipulator assemblies 102. The control device(s) 112 may include any number of a variety of input devices, such as joysticks, trackballs, data gloves, trigger-guns, hand-operated controllers, voice recognition devices, body motion or presence sensors, or the like.

In alternative embodiments, the robotic system may include more than one slave manipulator assembly and/or more than one master assembly. The exact number of manipulator assemblies will depend on the surgical procedure and the space constraints within the operating room, among other factors. The master assemblies may be collocated, or they may be positioned in separate locations. Multiple master assemblies allow more than one operator to control one or more slave manipulator assemblies in various combinations.

A visualization system 110 may include an endoscope system such that a concurrent (real-time) image of the surgical site is provided to surgeon console C. The concurrent image may be, for example, a two- or three-dimensional image captured by an imaging probe positioned within the surgical site. In this embodiment, the visualization system 110 includes endoscopic components that may be integrally or removably coupled to the surgical instrument 104. In alternative embodiments, however, a separate endoscope attached to a separate manipulator assembly may be used to image the surgical site. Alternatively, a separate endoscope assembly may be directly operated by a user, without robotic control. The endoscope assembly may navigation control devices include active steering devices (e.g., via teleoperated steeling wires) or passive steering devices (e.g., via guide wires or direct user guidance). The visualization system 110 may be implemented as hardware, firmware, software, or a combination thereof, which interacts with or is otherwise executed by one or more computer processors, including, for example the processor(s) of a control system 116.

A display system 111 may display an image of the surgical site and surgical instruments captured by the visualization system 110. The display 111 and the master control device(s) 112 may be oriented such that the relative positions of the imaging device in the scope assembly and the surgical instruments are similar to the relative positions of the surgeon's eyes and hand(s) so the operator can manipulate the surgical instrument 104 and the master control device(s) 112 as if viewing the workspace in substantially true presence. True presence means that the displayed tissue image appears to an operator as if the operator was physically present at the imager location and directly viewing the tissue from the imager's perspective.

Alternatively or additionally, display system 111 may present images of the surgical site recorded and/or modeled preoperatively using imaging technology such as computerized tomography (CT), magnetic resonance imaging (Mill), fluoroscopy, thermography, ultrasound, optical coherence tomography (OCT), thermal imaging, impedence imaging, laser imaging, nanotube X-ray imaging, or the like. The presented preoperative images may include two-dimensional, three-dimensional, or four-dimensional (including e.g., time based or velocity based information) images.

In some embodiments, the display system 111 may display a virtual navigational image in which the actual location of the surgical instrument is registered (e.g., dynamically, referenced) with previously recorded or concurrent images to present the surgeon S with a virtual image of the internal surgical site at the location of the tip of the surgical instrument.

In other embodiments, the display system 111 may display a virtual navigational image in which the actual location of the surgical instrument is registered with prior images (including preoperatively recorded images) or concurrent images to present the surgeon S with a virtual image of a surgical instrument at the surgical site. An image of a portion of the surgical instrument may be superimposed on the virtual image to assist the surgeon controlling the surgical instrument.

As shown in FIG. 1, a control system 116 includes at least one processor (not shown), and typically a plurality of processors, for effecting control between the slave surgical manipulator assembly 102, the master assembly 106, the visualization system 110, and the display system 111. The control system 116 also includes programmed instructions (e.g., a computer-readable medium storing the instructions)

to implement some or all of the methods described herein. While control system 116 is shown as a single block in the simplified schematic of FIG. 1, the system may comprise a number of data processing circuits (e.g., on the slave surgical manipulator assembly 102 and/or on the master assembly 106), with at least a portion of the processing optionally being performed adjacent the slave surgical manipulator assembly, a portion being performed the master assembly, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 116 supports wireless communication protocols such as Bluetooth, IrDA, HomeRF, IEEE 802.11 DECT, and Wireless Telemetry.

In some embodiments, control system 116 may include one or more servo controllers to provide force and torque feedback from the surgical instruments 104 to one or more corresponding servomotors for the control device(s) 112. The servo controller(s) may also transmit signals instructing manipulator assembly 102 to move instruments which extend into an internal surgical site within the patient body via openings in the body. Any suitable conventional or specialized servo controller may be used. A servo controller may be separate from, or integrated with, manipulator assembly 102. In some embodiments, the servo controller and manipulator assembly are provided as part of a robotic arm cart positioned adjacent to the patient's body.

Each manipulator assembly 102 supports a surgical instrument 104 and may comprise a serial kinematic chain of one or more non-servo controlled links (e.g., one or more links that may be manually positioned and locked in place, generally referred to as a set-up structure) and a robotic manipulator. The robotic manipulator assembly 102 is driven by a series of actuators (e.g., motors). These motors actively move the robotic manipulators in response to commands from the control system 116. The motors are further coupled to the surgical instrument so as to advance the surgical instrument into a naturally or surgically created anatomical orifice and to move the distal end of the surgical instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulatable end effector of the instrument for grasping tissue in the jaws of a biopsy device or the like.

Figure 2:
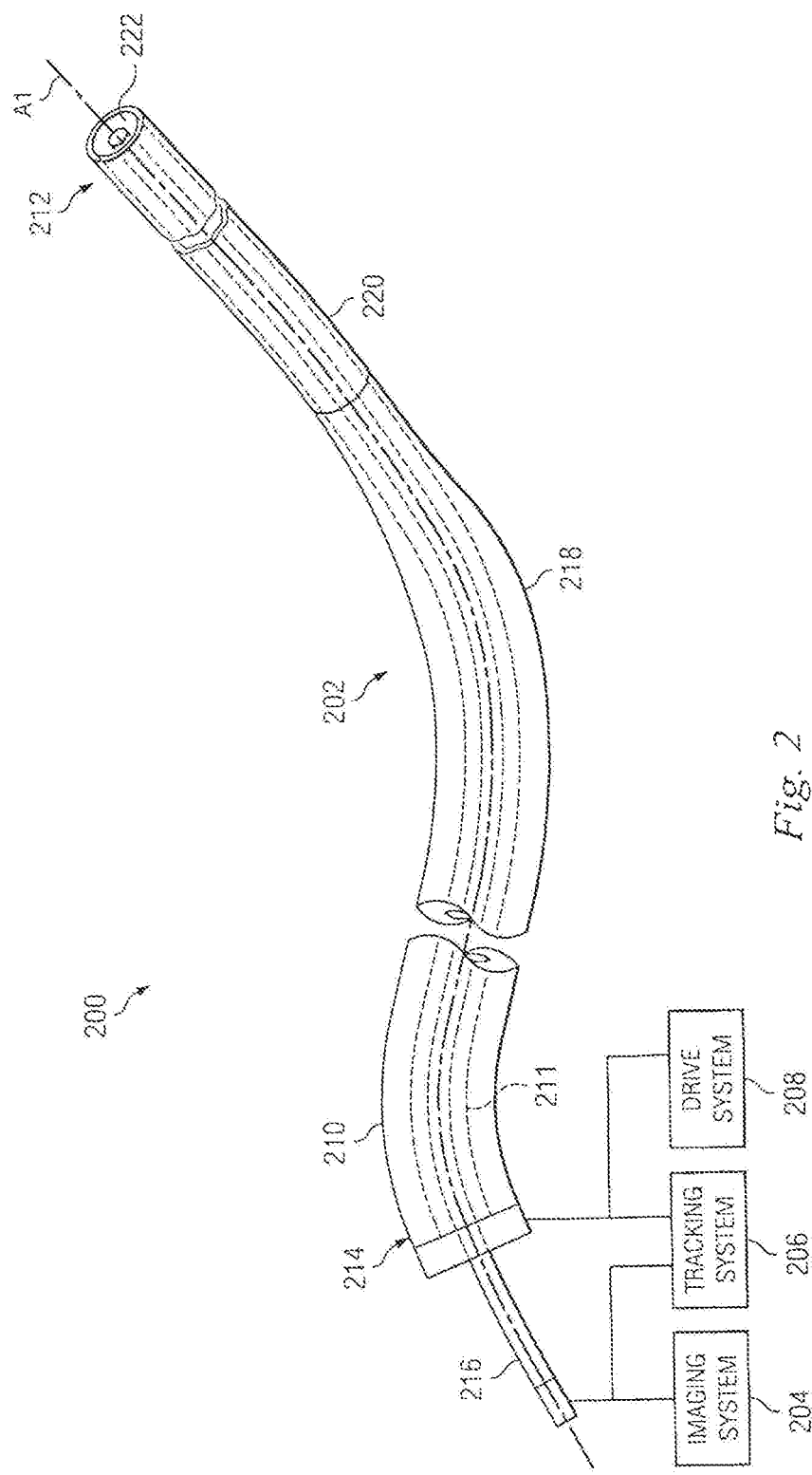
FIG. 2 illustrates an endoscopy system utilizing aspects of the present disclosure.

FIG. 2 illustrates a minimally invasive surgical system 200 utilizing aspects of the present disclosure. The system 200 includes a minimally invasive assembly 202, an imaging system 204, a tracking system 206, and a drive system 208. The minimally invasive surgical system 200 may be incorporated into a robotic surgical system, such as system 100 (e.g., as part of instrument 104), as part of the visualization and display system. Alternatively, the minimally, invasive surgical system 200 may be used for non-robotic exploratory procedures or in procedures involving traditional manually operated surgical instruments, such as laparoscopic instruments without robotic control (e.g., systems in which drive system 208 includes handles, triggers, or other interface elements for directly manipulating catheter 210), or "hybrid" procedures in which both robotic and non-robotic controls are provided and/or employed.

The minimally invasive assembly 202 includes an elongated flexible catheter 210 having a distal end 212 and a proximal end 214. The catheter 210 includes a body wall 211 which defines a central operational passageway 222 through the catheter 210. A central axis A1 extends longitudinally through the central operational passageway 222. The passageway 222 is sized to receive an operational component such as a flexible probe 216. The flexible probe 216 may be, for example, an imaging probe.

The flexible catheter 210 includes a passively flexible portion 218 and a steerable flexible portion 220. As the catheter 210 is advanced through an anatomical lumen, the passive portion 218 bends or curves passively in response to external forces. The steerable portion 220 includes an integrated mechanism for operator control of instrument bending as will be described further below.

The passive portion 218 can have an outer diameter that is larger than the outer diameter of the steerable portion 220, for example to accommodate components in the passive portion that do not extend into the steerable portion, as described further below. In one example, the outer diameter of the passive portion may be approximately 5 mm. The smaller diameter of the steerable portion 220 can allow it to navigate smaller body lumens that may not be accessible by the proximal body portion. In another example, the outer diameter of the steerable portion may be approximately 3 mm.

During a minimally invasive surgical procedure, accurate registration of the probe (e.g., an imaging probe) to images of a patient anatomy (including prerecorded, schematic, or concurrent images) relies upon assumptions about the position and relative motion of sensors and other components associated with the probe and its guiding catheter. For the assumptions to be accurate, a precise determination of the relative sensor poses is desirable. As described below, the structure of the guide catheter and the probe can limit the relative motion of sensors, catheter steering devices, and imaging components to provide consistent and reliable information about the relative sensor poses, positions, and/or orientations.

FIGS. 3a, 3b, 3c, 3d, and 3e illustrate a probe assembly 250 including an elongated flexible catheter 252 with a body wall 254 defining a central operational passageway 256 through the catheter. A central axis A2 extends longitudinally through the central operational passageway 256. The passageway 256 is sized to receive a flexible probe 258. The catheter 252 includes a passively flexible portion 260, a steerable flexible portion 262, a proximal alignment support structure 264 and a distal alignment support structure 265. In this embodiment, the alignment support structures 264, 265 of the catheter 252 are precision machined, molded, or otherwise manufactured to control the relative position/alignment of various sensors and steering wires, thus reducing the geometric variability that could otherwise occur during manufacturing and/or use of catheter 252. Reducing this variability improves the accuracy of the pose and shape calculations that rely upon assumptions about the relative locations of the sensors and steering wires. In alternative embodiments, a single support structure, either at the proximal or distal end of the steering portion may be used.

In this embodiment, the proximal support structure 264 and the portions 260, 262 of the catheter 252 are serially aligned, with the proximal support structure coupled between the passive portion 260 and the steerable portion 262. For example, one end of the proximal support structure 264 may abut or overlap the distal end of the passive portion 260 and the other end may abut or overlap the proximal end of the steerable portion 262. In alternative embodiments, the proximal support structure 264 may be a ring that slides over and becomes affixed to a distal section of the passive portion 260. Other constructions that fix the proximal support structure 264 relative to the passive portion 260 and the steerable portion 262 may also be suitable. Although in certain specific embodiments the support structures may be coupled to the passive and steerable portions as described, in other embodiments, the support structures may be positioned anywhere along the catheter. In various embodiments, the support structures 264, 265 may be integrated within, affixed on, or otherwise mounted to the catheter 210.

As shown in FIG. 3*b*, the proximal support structure 264 includes a body wall portion 267. The support structure 264 includes alignment features that can be used to fix the position and orientation of operational components, such as sensors and/or steering wires that extend within the support structure. For example, a passageway 266 extends longitudinally through or partially through the body wall 267. The passageway 266 is radially offset from and generally parallel to the central axis A2. The passageway 266 is sized to mate with a sensor component 268 which may extend the length of or a partial length of the support structure 264. Sensor component 268 can be glued, press-fit, or otherwise fixed within at least a portion of passageway 266, thereby precisely positioning and orienting sensor component 268 within support structure 264. As used herein, the term "fixed" is generally used to describe a position or orientation that varies within a limited range during normal catheter and probe use. Note that while passageway 266 is depicted and described as an alignment feature for sensor component 268, in various other embodiments, such alignment feature can include a notch, groove, ridge(s), pocket, or any other feature within or on an internal/external surface of body wall 267.

The support structure 264 further includes alignment features such as navigation passageways 270 sized to receive navigation control devices, such as steering wires 272. The passageways 270 are radially offset from and generally parallel to the central axis A2. In this embodiment, the passageways 270 are generally evenly spaced in a radial pattern about the axis A2, in alternative embodiments, there may be fewer or more passageways 270 to accommodate fewer or more steering wires, and the passageways may be in various symmetric or non-symmetric configurations, at equal or varying radial distances from axis A2. Steering wires 272 are slidably mated within the passageways 270, which constrain the position and orientation of the steering wires within support structure 264. Note that while passageways 270 are depicted and described as alignment features for the steering wires 272, in various other embodiments, such alignment feature can include a notch, groove, ridge(s), pocket, or any other feature within or on an internal/external surface of body wall 267.

The proximal support structure 264 can also include a passageway 274 sized to mate with a sensor component 276. The passageway 274 is radially offset from and generally parallel to the axis A2. The sensor component 276 may be glued or otherwise fixed at least partially within the passageway 274 to limit movement in one or more degrees of freedom, including lateral movement (e.g., in the X-Y coordinate plane), longitudinal movement (e.g., in the Z-coordinate direction), and roll (e.g., about the Z-coordinate direction) of the sensor component 276 relative to the proximal support structure 264. In another embodiment, the sensor component 276 may have cross section shaped like a key structure that matches a key-hole shape in passageway 274 to limit the roll movement (e.g., rotation around the Z-coordinate direction) of the sensor 276 relative to the proximal support structure 264. Note that while passageway 274 is depicted and described as an alignment feature for the sensor component 276, in various other embodiments, such alignment feature can include a notch, groove, ridge(s), pocket, or any other feature within or on an internal/external surface of body wall 267.

Thus, passageways 266, 270, and 274 control the positioning and orientation of sensor component 268, steering wires 272, and sensor component 276 relative to each other within support structure 264. Furthermore, passageways 266, 270, and 274 control the positioning and orientation of sensor component 268, steering wires 272, and sensor component 276 relative to central axis A2. Therefore, by accurately manufacturing support structure 264, the positioning and orientation (at support structure 264) of sensor component 268, steering wires 272, and sensor component 276 relative to each other and/or central axis A2/central operational passageway 256 can be accurately characterized and controlled within catheter 210. This precise positional and orientation control in turn enables accurate sensor monitoring and catheter control, due to the close correlation between the actual positions/orientations of sensor component 268, steering wires 272, and sensor component 276 (relative to each other and/or central axis A2) and the expected positions/orientations used in the algorithms for controlling and/or detecting position, shape, and/or pose of catheter 210. The proximal support structure 264 may be formed of a material sufficiently rigid to maintain the fixed spatial displacements of the passageways 266, 270, and 274. Suitable materials may include metals, rigid polymer materials, or ceramics. The proximal support structure 264 is generally more rigid than the flexible catheter portions 260, 262. In many embodiments, the rigidity and the generally shorter length of support structure 264 relative to catheter portions 260 and 262 can allow support structure 264 to be produced with significantly tighter dimensional tolerances than would be possible within catheter portions 260 and 262, thereby enabling greater placement accuracy of sensor component 268, steering wires 272, and sensor component 276 within catheter 210 than would be possible from relying on features within catheter portions 260 and 262.

In this embodiment, the distal support structure 265 is coupled to the distal end of the steerable portion 262. For example, the proximal end of the distal support structure 265 may abut or overlap the distal end of the steerable portion 262. In alternative embodiments, the distal support structure 265 may be a ring that slides over or into and becomes affixed to a distal section of the steerable portion 262. Other constructions that fix the distal support structure 265 relative to the steerable portion 262 may also be suitable.

As shown in FIG. 3*c*, the distal support structure 265 includes a body wall portion 278. The support structure 265 includes alignment features that can be used to fix the position and orientation of operational components, such as sensors and/or steering wires that extend within the support structure. For example, the distal support structure 265 further includes navigation passageways 280 sized to mate with the navigation control devices, such as the steering wires 272. The passageways 270 are radially offset from and generally parallel to the central axis A2. In this embodiment, the passageways 280 are generally evenly spaced in a radial pattern about the axis A2. In alternative embodiments, there may be fewer or more passageways 280 to accommodate fewer or more steering wires, and the passageways may be in various symmetric or non-symmetric configurations, at equal or varying radial distances from axis A2. Steering wires 272 are positioned within passageways 280, which constrain the position and orientation of the steering wires within support structure 265. In some embodiments, steering wires can be secured within passageways 280 (e.g., via adhesive, soldering, clamping, or attached to attachment features within or around passageways 280). In other embodiments, steering wires can be secured to support structure 265 at a location outside of passageways 280.

The distal support structure 265 also includes a sensor alignment feature, such as a passageway 282 sized to mate with the sensor component 276. The passageway 282 is radially offset from and generally parallel to the axis A2. The sensor component 276 may be glued or otherwise fixed at least partially within the passageway 282 to limit movement in at least one degree of freedom including for example, lateral movement (e.g., in the X-Y coordinate plane) longitudinal movement (e.g., in the Z-coordinate direction), and roll (e.g., about the Z-coordinate direction) of the sensor component 276 relative to the distal support structure 264.

Thus, passageways 280, 282 control the position and orientation of steering wires 272 and sensor component 276 relative to each other within support structure 265. Furthermore, passageways 280 and 282 control the positioning and orientation of steering wires 272 and sensor component 276 relative to central axis A2. Therefore, by accurately manufacturing support structure 265, the positioning and orientation (at support structure 265) of steering wires 272 and sensor component 276 relative to each other and/or central axis A2/central operational passageway 265 can be accurately characterized and controlled within catheter 210. In a similar manner to that noted above with respect to support structure 264, this precise positional and orientation control in turn enables accurate sensor monitoring and catheter control, due to the close correlation between the actual positions/orientations of steeling wires 272 and sensor component 276 (relative to each other and/or central axis A2) and the expected positions/orientations used in the algorithms for controlling and/or detecting position, shape, and/or pose of catheter 210. The distal support structure 265 may be formed of a material sufficiently rigid to maintain the fixed spatial displacements of the passageways 280, 282. Suitable materials may include metals, rigid polymer materials, or ceramics. The distal support structure 265 is generally more rigid than the flexible catheter portions 260, 262. Because the support structures 264, 265 are generally more rigid than the rest of the catheter, locating them in limited locations, such as at proximal and distal ends of the steerable portion of the catheter 252, allows greater flexibility and steerability for the length of the steerable portion of the catheter between the support structures. Furthermore, in many embodiments, the rigidity and the generally shorter length of support structure 265 relative to catheter portion 262 can allow support structure 265 to be produced with significantly tighter dimensional tolerances than would be possible within catheter portion 262, thereby enabling greater placement accuracy of steering wires 272, and sensor component 276 within catheter 210 than would be possible from relying on features within catheter portions 260 and 262.

Figure 3D:
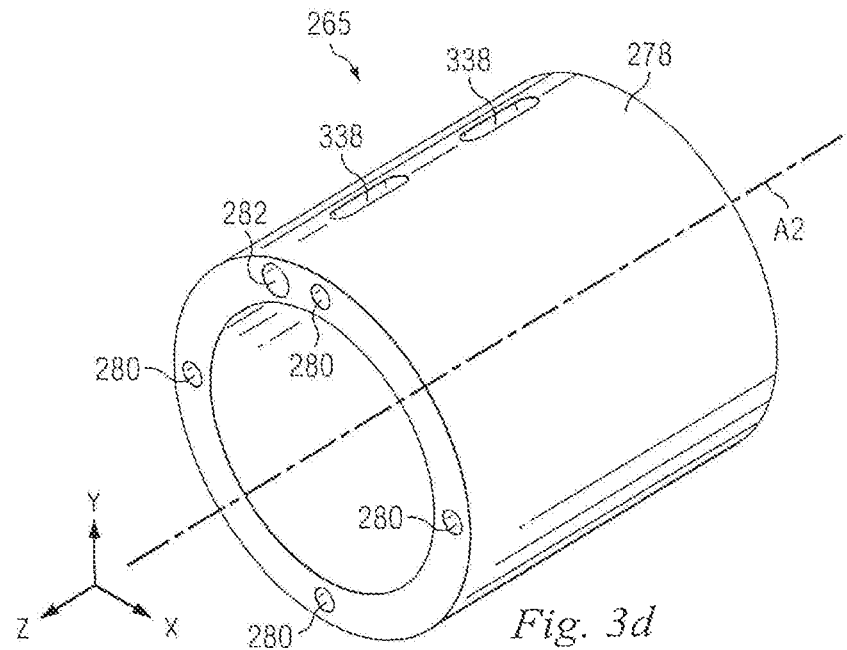
FIG. 3d is a perspective view of the alignment support structure of FIG. 3c.

As shown in FIG. 3d, the distal support structure 265 can further include ports 338 through which an adhesive material (not shown) may be placed to adhere the sensor component 276 to the support structure 265 to fix the sensor component relative to the support structure.

The proximal support structure 264 has an outer diameter D1, and the distal support structure 265 has an outer diameter D2. The diameter D1 is generally larger than the diameter D2 to accommodate the sensor 268 that extends within the proximal support structure 264. The passageways 280, 282 extend through the body wall portion 265 with the same radial spacing from the axis A2 as the respective passageways 270, 274 in the proximal support structure 264. Alternatively, the passageways 280, 282 in the distal support structure 265 may be spaced a different predetermined distance from the axis A2. For example, they may be spaced closer to the axis A2 to accommodate the smaller diameter of the steerable portion 265.

The overall length of the catheter 252 may be approximately 60 to 80 cm, although longer or shorter catheters may be suitable. The steerable body portion 262 may have a length of approximately 10 to 20 cm. In various embodiments, the lengths of the steerable and passive portions of the catheter 252 may be longer or shorter.

The passive flexible portion 260 of the catheter 252 may have an extruded construction with channels for the operational passageway 256, the steering wires 272, and/or the sensors 268, 276. Similarly, the distal flexible portion 262 of the catheter 252 may have an extruded construction with channels for the operational passageway 256, the steering wires 272, and/or the sensor 276. Alternatively, the flexible portions 260, 262 may have a multilayer construction (e.g., a set of coaxial catheters sandwiching tubes to direct the steering wires or sensors).

The steering wires 272 extend through the passive portion 260 of the catheter 252, through the passageways 270 of the proximal support structure 264, and through the steerable portion 262 of the catheter 252. The steering wires 272 may terminate in the passageways 280 of the distal support structure 265 or in a portion of the catheter 252 (not shown) that extends distally of the support structure 265. Similarly, the sensor component 276 extends through the passive portion 260 of the catheter 252, through the passageway 274 of the proximal support structure 264, and through the through the steerable portion 262 of the catheter 252. The sensor 276 may terminate in the passageway 282 of the distal support structure 265 or in a portion of the catheter 252 (not shown) that extends distally of the support structure 265. The sensor component 268 extends through the passageway 266 of the proximal support structure 264 but may be terminated proximally of steerable portion 262 to allow the steerable portion to navigate smaller anatomical body passageways.

The steering wires 272 are controlled by a drive system (e.g. the drive system 208). The drive system 208 may be incorporated as part of manipulator 102. Examples of drive systems and flexible surgical instruments with remote control steering mechanisms are described in U.S. Pat. No. 7,942,868, filed Jun. 13, 2007, entitled "Surgical Instrument With. Parallel Motion Mechanism;" U.S. Pat. App. Pub. No. 2010/0331820, filed Jun. 30, 2009, entitled, "Compliant Surgical Device;" and U.S. Pat. App. Pub. No. 2010/0082041, filed Sep. 30, 2008, entitled "Passive Preload and Capstan Drive for Surgical instruments," the full disclosures of which are all incorporated by reference herein in their entirety. In various alternatives, the catheter 252 may be non-steerable with no integrated mechanism for operator control of the instrument bending, in which case, the steering wires 272 and their associated passageways may be omitted.

In this embodiment, the sensor component 268 can be an electromagnetic (EM) sensor component that includes one or more conductive coils that may be subjected to an externally, generated electromagnetic field. Each coil of the EM sensor component 268 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point. These measurements are gathered by a tracking system e.g., tracking system 206). Alternatively the EM sensor system may sense fewer degrees of freedom. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety. If implemented as a six-degree of freedom EM sensor, size constraints may limit placement of sensor component 268 to the passive portion 260 of catheter 252 (e.g., within or adjacent to proximal support structure 264) to allow the diameter of steerable portion 262 to be minimized for accessing smaller body lumens.

The sensor component 276 can include an optical fiber extending at least partially within the passageways 274, 282. The tracking system 206 is coupled to a proximal end of the sensor component 276. In this embodiment, the fiber has a diameter of approximately 200 μm. In other embodiments, the dimensions may be larger or smaller.

The optical fiber of the sensor component 276 forms a fiber optic bend sensor for determining the shape of the steerable catheter portion 262. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional patent application Ser. No. 12/047,056, filed on Aug. 10, 2010, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable.

In this embodiment, the optical fiber of the shape sensor 276 may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres of Bracknell, England. Use of FBG technology in position sensors for robotic surgery is described in U.S. Pat. No. 7,930,065, filed Jul. 20, 2006, disclosing "Robotic Surgery System including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber.

As described, the optical fiber of the shape sensor 276 is used to monitor the shape of the steerable portion 262 of the catheter 252. More specifically, light passing through the optical fiber is processed by the tracking system 206 for detecting the shape of the portion 262 and for utilizing that information to assist in surgical procedures. The tracking system 206 may include a detection system for generating and detecting the light used for determining the shape of the catheter portion 262. This information, in turn, in can be used to determine other related variables, such as velocity and acceleration of the parts of a surgical instrument. By obtaining accurate measurements of one or more of these variables in real time, the controller can improve the accuracy of the robotic surgical system and compensate for errors introduced in driving the component parts. The sensing may be limited only to the degrees of freedom that are actuated by the robotic system, or may be applied to both passive (e.g., unactuated bending of the rigid structures between joints) and active (e.g., actuated movement of the instrument) degrees of freedom.

Figure 3E:
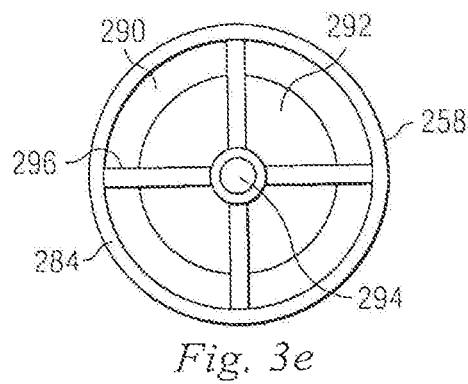

The probe 258 is sized to extend through the passageway 256 of the catheter 252 to capture images of the patient anatomy distal of the catheter. The probe 258 includes an elongated flexible body 284 having a proximal end 286 and a distal end 288 which includes a distal tip. In one embodiment, the flexible body 284 has an approximately 2 mm outer diameter. In other embodiments, the flexible body 284 outer diameter may be larger or smaller. The flexible body 284 may be formed from a transparent, semi-transparent, or opaque material. The flexible body 284 includes a channel 290 that runs longitudinally along at least a portion of the length of the flexible body. An image capture instrument 292 extends within the channel 290. A sensor component 294 also extends through the channel 290. As shown in FIG. 3e, the probe 258 optionally includes an alignment support structure such as rigid alignment frame 296 through which the sensor component 294 extends. The alignment frame 296 may extend within a portion of the channel 290 and is supported by the body 284. Similar to the alignment support structures, the rigid frame 296 controls the placement of the sensor component 294 relative to the body 284 and relative to the image capture instrument 292. In this embodiment, the sensor component 294 is generally axially aligned with the image capture instrument 292 along the central axis A2 of the body 284 and is positioned proximally of the image capture instrument. The sensor component 294 may be adhered to the frame 296 to prevent movement. Optionally, other operational components, such as illumination devices or discrete fluid conduits (not shown), may extend within the channel 290. In one aspect, the remaining portion of the channel 290, not occupied by the instrument 292 or any other operational components, may be a flow channel for delivering fluid to or from the distal end 288 of the probe 258. Further description of various embodiments of probes are described in U.S. Provisional Application No. 61/658, 305, filed Jun. 11, 2012, entitled "Systems and Methods for Cleaning a Minimally Invasive Instrument," which is incorporated by reference herein in its entirety.

The image capture instrument 292 includes a stereoscopic or monoscopic camera disposed near the distal end 288 of the flexible body 284 for capturing images that are transmitted to and processed by an imaging system (e.g., imaging system 204) for display. The imaging system 204 may be incorporated as part of visualization system 110 and display system 111. The image capture instrument 292 includes cabling and various mechanical, optical, and electrical couplings (not shown) for interfacing with the imaging system 204. Alternatively, the image capture instrument may be a coherent fiber-optic bundle, such as a fiberscope, that couples to the imaging system. The image capture instrument may be single or multi-spectral, for example capturing image data in the visible spectrum, or capturing image data in the visible and infrared or ultraviolet spectrums. In other various alternatives, the image capture instrument 292 may wirelessly communicate image data to the imaging system 204.

The sensor component 294 can be an EM sensor component that includes one or more conductive coils that may be subjected to an externally generated electromagnetic field. Each coil of the EM sensor component 294 then produces an induced electrical signal having characteristics that depend on the position and orientation of the coil relative to the externally generated electromagnetic field. In one embodiment, the EM sensor system may be configured and positioned to measure five degrees of freedom of a base point. These measurements are gathered by the tracking system 206. Alternatively the EM sensor system may sense fewer or more degrees of freedom. Further description of an EM sensor system is provided in the previously incorporated by reference U.S. Pat. No. 6,380,732. The five degree-of-freedom EM sensor component 294 may be smaller than the six degree-of freedom EM sensor 268, thus permitting the probe 258 to have a diameter small enough to extend through the passageway 256 of the catheter 252.

The tracking system 206 can use information received from the catheter EM sensor component 268, the shape sensor component 276, and optionally the probe sensor component 294 in determining the position, orientation, speed, pose, and/or shape of the steerable portion 262 of the catheter 252, the image capture instrument 292, a distal tip of the probe 258, and/or other components or portions of the catheter 252, The tracking system 206 may be implemented as hardware, firmware, software or a combination thereof which interact with or are otherwise executed by one or more computer processors, which may include the processors of a control system 116.

The information from the tracking system 206 may be combined with concurrent information from the visualization system 110 and/or the previously recorded patient images to provide the surgeon or other operator with real-time position information on the display system 111 for use in the control of the system 250. The control system 116 may utilize the position information as feedback for positioning the catheter 252, Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for image-Guided Surgery," which is incorporated by reference herein in its entirety.

Any geometric variability in the relative separation between the various sensors or between the sensors and the steering wires affects the accuracy of the pose and shape information calculated using the combined data from the EM sensors and the shape sensor, Inaccuracies in the pose and shape information may cause errors in the control signals subsequently provided to move the steering wires. These inaccuracies may further cause error in the registration of the catheter and probe to anatomical images of the patient. The passageways in the proximal and distal support structures 264, 265 of the catheter 252 and the frame 296 of the probe 258 tightly control the relative geometrical placement of the sensors 268, 276, 294 and the steering wires 272. Controlling the relative alignment of the sensors and the steering wires reduces the geometric variability that would otherwise occur as the catheter and probe are maneuvered through tortuous anatomical lumens. Reducing this variability may improve the accuracy of the pose and shape calculations that rely upon assumptions about the relative locations of the sensors and steering wires.

Accurate registration of the catheter 252 and probe 258 to images of a patient anatomy (including prerecorded, schematic, or concurrent images) are based upon assumptions about the position of the sensors 268, 276, 294 and the relative motion of the sensors. For the assumptions to be accurate, the relative sensor poses should be accurately determined. As described above, the construction of the support structures 264, 265 with dedicated passageways and the probe 258 with frames, serves to provide reliable information about the relative sensor poses, positions, and/or orientations.

In the embodiment described above, to provide reliable information, the shape sensor component 276 may be held in a fixed lateral position relative to the catheter 252. Further, the shape sensor component 276 may be maintained in a fixed pose relative to the sensor component 268, although longitudinal sliding may be permitted. Additionally, the shape sensor component 276 may be maintained in a fixed pose relative to the distal end and particularly the distal tip of the catheter 252. Further, the sensor component 294 may be maintained in a fixed pose relative to the distal tip of the probe 258 and is generally aligned collinearly with the central axis of the probe (which is collinear with axis A2 when the probe 258 is inserted into the operational passageway 256. Alternatively, the sensor component 294 may be disposed in a different known configuration within the probe 258, such as parallel to the central axis of the probe. In alternative embodiments, the sensor components of the probe or catheter may be held in fixed positions, orientations, or poses relative to various locations on the catheter, probe, or specific operational components of the catheter or probe. Further, the sensor components may be held in alignment with various other operational components of the catheter or probe.

The mechanical tolerances for the passageways of the support structures and the frame of the probe may vary depending upon the needed accuracy. In various specific embodiments, suitable tolerances are described below. For example, in various embodiments, the shape sensor component 276 may be maintained in a fixed position (e.g., less than approximately 1 mm variation) and fixed orientation (e.g., less than approximately 1 degree of rotation variation) at a point of the shape sensor component closest to the EM sensor component 268. In various embodiments, the same positioning/orientation of the shape sensor component 276 relative to steering wires 272 at the distal end region of catheter 250 can be maintained by support structure 265. In various embodiments, the shape sensor component 276 may be maintained in a fixed lateral position (e.g., less than approximately 0.5 mm variation) and pitch/yaw orientation (e.g, less than approximately 0.5 degree of rotation variation) relative to the EM sensor component 268. In various embodiments, the amount of roll induced on the shape sensor component 276 between the EM sensor component 268 and the tip of the catheter 252 may be maintained at less than approximately 5 degrees during articulation. For example, the sensor component 276 may have cross section shaped like a key structure that matches a key-hole shape in passageways 274/282 to limit the roll movement (e.g., rotation around the Z-coordinate direction) of the sensor 276. In various embodiments, the distal end of the shape sensor component 276 may be maintained at a fixed position (e.g., approximately less than 0.5 mm variation) approximately 2 mm or less from the distal tip of the catheter. In various embodiments, the EM sensor component 294 may be maintained in a fixed position (e.g., less than approximately 1 mm variation) and fixed orientation (e.g., less than approximately 10 degrees of variation) relative to the distal end of the probe 258. In various embodiments, the longitudinal axis of the EM sensor component 294 may be fixed collinearly (e.g., within approximately less than 0.5 mm and approximately less than 5 degrees of variation) with the central axis of the probe. In various embodiments, the shape sensor component 276 may have a lateral position relative to the steering wires that varies less than approximately 1 mm. In various embodiments, the shape sensor component 276 may have a lateral distance relative to the EM sensor component 268 that varies less than approximately 1 mm. In various embodiments, the shape sensor component 276 may have a lateral position relative to the distal tip of the catheter 252 that varies by less than approximately 1 mm.

In various alternative embodiments, the alignment support structures may be integrated with the catheter. For example, a section of the catheter near the steerable portion (e.g., immediately distal or proximal of the steerable portion) may be precision extruded or precision machined to form tightly tolerance passageways in the catheter. Alternatively, rigid support structures may be inserted into the catheter for fixing the sensor components. The inserted support structures may be held in place by an adhesive, a friction fit, or other known methods of adherence.

Figure 4:
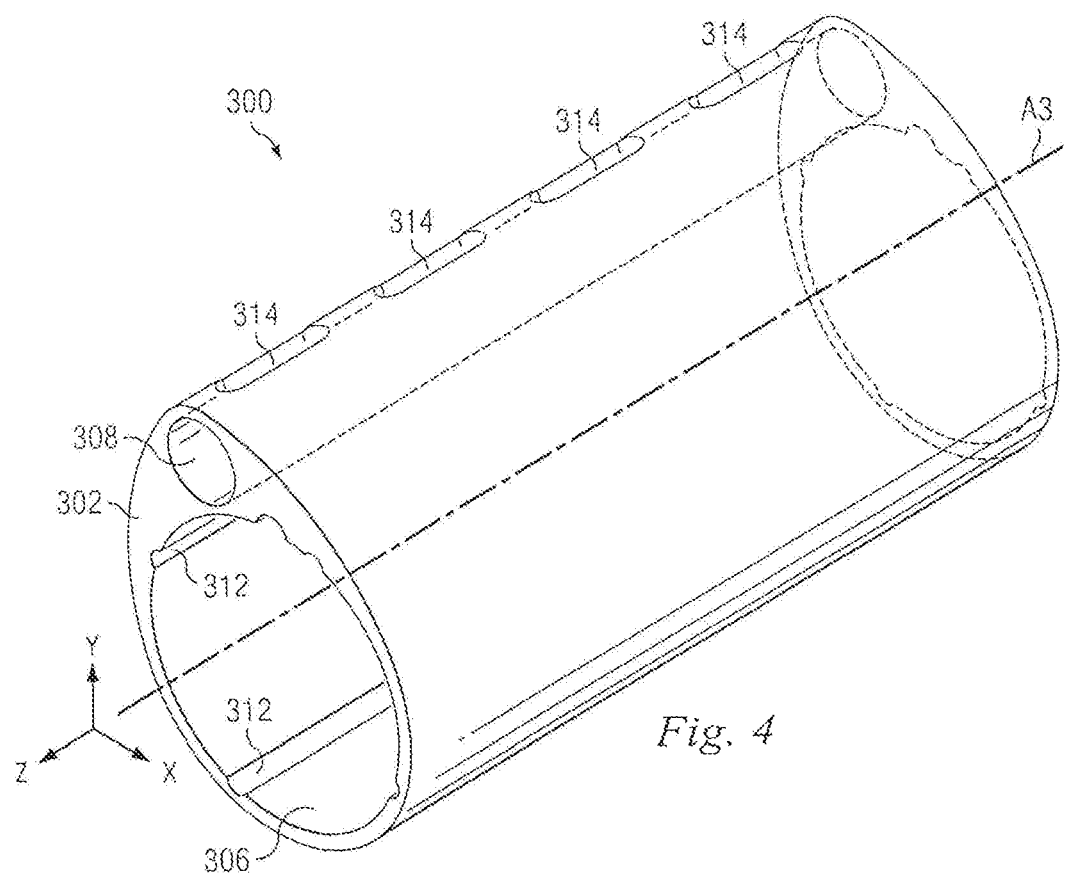
FIG. 4 is a perspective view of an alternative proximal support structure according to an embodiment of the disclosure.
Figure 5:
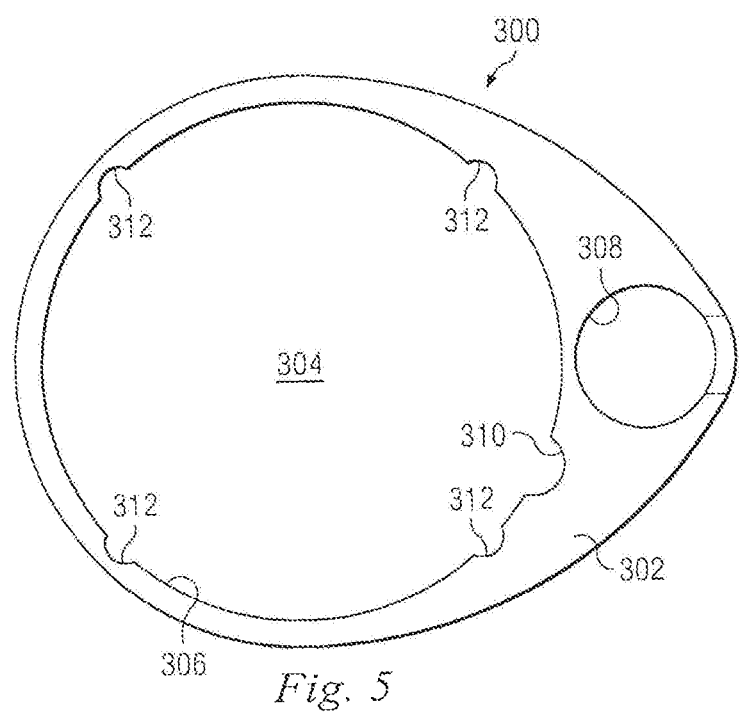
FIG. 5 is an end view of the proximal support structure of FIG. 4

An alternative embodiment of a proximal support structure is illustrated in FIGS. 4 and 5. In this embodiment, a proximal support structure 300 has a body wall 302 through which a passageway 304 extends. The passageway 304 includes a circumferential boundary 306 and is sized for through passage of a probe (e.g., probe 258) and is centrally aligned about an axis A3. A passageway 308 extends through the body wall 302 and is radially offset from and generally parallel to the axis A3. The passageway 308 is sized to mate with a sensor component such as sensor component 268. The support structure 300 further includes a groove 310 sized to mate with the sensor component 276. The groove 310 may generally retain the sensor component 276 near the circumferential boundary 306, limiting or restricting lateral motion (X-Y coordinate directions) of the sensor component within the passageway 304. The sensor component 276 may slide or rotate within the groove 310. The support structure 300 further includes grooves 312 sized to receive steering wires 272. The grooves 312 may generally retain the steering wires 272 near the circumferential boundary 306, limiting or restricting lateral motion of the sensor component within the passageway 304 toward the axis A3 or radially about the axis A3. The steering wires 272 may slide or rotate within the grooves 312. The support structure 300 may further include ports 314 through which an adhesive material (not shown) may be placed to adhere the sensor component 268 to the support structure 300 to prevent or limit motion of the sensor component relative to the support structure. Note that while various grooves (310, 312) and passageways (304) are depicted and described as an alignment features for exemplary purposes, in various other embodiments, such alignment features can include any combination of passageways, notches, grooves, ridges, pockets, or any other features within or on an internal/external surface of body wall 302.

Figure 6:
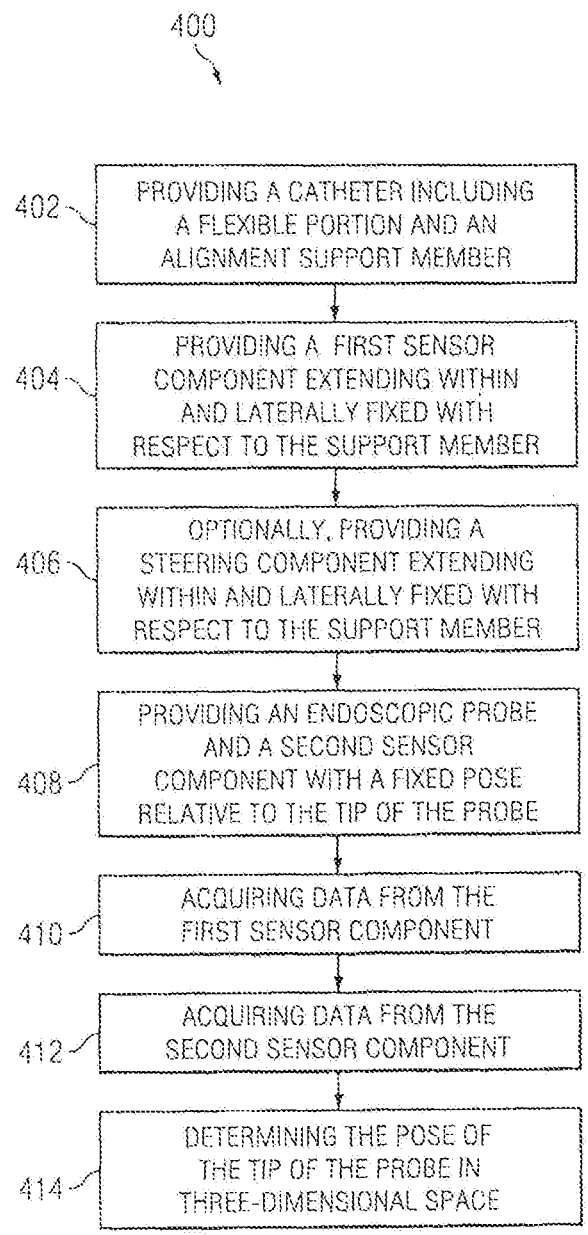
FIG. 6 is a flowchart describing a method for determining the pose of a portion of a probe in three-dimensional space.

Referring now to FIG. 6, a method 400 of operating an endoscopy system includes at 402, providing a catheter with an alignment support structure. The method also includes at 404, providing a first sensor component extending within and laterally fixed with respect to the support structure. Optionally, at 406, a steering component, such as steering wires, are provided to extend within the support structure. The steering wires are laterally fixed with respect to the support structure. At 408, a probe is provided. A second sensor component extends within the probe and has a fixed pose relative to the tip of the probe. The method 400 includes, at 410, acquiring data from the first sensor component. At 412, data is acquired from the second sensor component. At 414, the pose of the distal tip of the probe, in three-dimensional space, is determined with the data from the first and second sensor components. In some embodiments, the determination of 414 is performed using a relative position and/or orientation of the first and second sensors (with respect to each other and/or with respect to a central axis of the catheter) defined by the support structure. The pose of the distal tip of the probe can be registered with an image of the patient anatomy to provide the surgeon with accurate navigation information for moving the catheter and probe within the patient anatomy.

FIG. 7 illustrates a distal end of a probe 500 according to an embodiment of the disclosure. The probe 500 may be used as an alternative to probe 258 for use within the system 250. The probe 500 is similar to the probe 258, with the differences to be described. In this embodiment, the probe 500 includes an elongated flexible body 502. The flexible body 502 includes a longitudinal channel 504 in which an image capture instrument 506 extends. A sensor component 508 also extends through the channel 504. The sensor component 508 is illustrated schematically and may be positioned in any of a variety of ways within the channel 504.

The probe 500 optionally includes support structures within the channel to support the image capture instrument and/or sensor component 508 in a fixed lateral position within the channel. The support structures may be constructed to hold the sensor component 508 and the image capture instrument 506 in different spatial relationships relative to each other or to the body 502, including coaxial, non-coaxial, parallel alignments or angled relationships. Optionally, other operational components, such as illumination devices or discrete fluid conduits (not shown), may extend within the channel 504. Further description of various components and embodiments of probes are described in the previously incorporated by reference U.S. Provisional Application No. 61/658,305.

Although the systems and methods have been described herein with respect to endoluminal probes, the systems and methods are also suitable for other applications in which in vivo cleaning of an instrument is advantageous. For example, the fluid delivery and cleaning systems and methods described may be suitable for use with ablation catheters, laser fibers, other minimally invasive instruments, or other types of endoscopic devices.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any, particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely, illustrative of and not restrictive on the broad invention, and that the embodiments of the invention not be limited to the specific constructions and arrangements shown and described, since various other modifications may occur to those ordinarily skilled in the art.

What is claimed is:

1. A catheter system, comprising:
an elongate flexible catheter;
a support structure mounted on a distal portion of the elongate flexible catheter, the support structure including:
a first alignment feature configured to mate with a sensor such that the sensor is maintained parallel to a longitudinal axis of the support structure; and
a second alignment feature configured to mate with a navigation control device such that the navigation control device is fixed relative to the sensor in at least one degree of freedom.

2. The catheter system of claim 1, wherein a cross section shape of the sensor is configured to mate with a matching shape in the first alignment feature.

3. The catheter system of claim 1, wherein the navigation control device comprises a steering wire.

4. The catheter system of claim 1, wherein the sensor is glued or press-fit to at least a portion of the first alignment feature.

5. The catheter system of claim 1, wherein the sensor extends partially within the support structure.

6. The catheter system of claim 1, wherein the sensor extends through the support structure.

7. The catheter system of claim 1, wherein the first sensor comprises a shape sensor.

8. The catheter system of claim 1, wherein the first alignment feature includes a passageway extending through the support structure, the support structure further including a port that couples an exterior surface of the support structure to an interior surface of the passageway of the first alignment feature.

9. The catheter system of claim 1, further comprising:
a second support structure comprising a third alignment feature configured to mate with the sensor and having an outer diameter that is larger than an outer diameter of the support structure.

10. The catheter system of claim 1, wherein the support structure comprises an operational passageway extending along a central axis, the operational passageway configured to receive a probe, wherein the first and second alignment features are radially offset from and parallel to the central axis.

11. The catheter system of claim 10, further comprising the probe, wherein the probe includes a sensor component.

12. The catheter system of claim 11, wherein the probe further includes an alignment frame supporting the sensor component in a fixed pose relative to an image capture instrument.

13. The catheter system of claim 12, further comprising a tracking system configured to receive first sensor data from the sensor and second sensor data from the sensor component and to determine a pose of a distal tip of the probe based on the first and second sensor data.

14. The catheter system of claim 1, wherein a proximal surface of the support structure is coupled to a distal surface of the distal portion of the elongate flexible catheter.

15. The catheter system of claim 1, wherein the support structure comprises a ring configured to fix the support structure to the distal portion of the elongate flexible catheter.

16. The catheter system of claim 1, wherein a proximal portion of the elongate flexible catheter comprises a passive portion and the distal portion of the elongate flexible catheter comprises a steerable portion.

17. A catheter system, comprising:
a first support structure mounted on a distal portion of an elongate flexible catheter, the first support structure including:
a first alignment feature configured to mate with a first sensor such that the first sensor is maintained parallel to a longitudinal axis of the first support structure; and
a second alignment feature configured to mate with a navigation control device such that the navigation control device is maintained parallel to the longitudinal axis of the first support structure and fixed relative to the first sensor in at least one degree of freedom; and
a second support structure mounted on a proximal portion of the elongate flexible catheter, the second support structure including:
a third alignment feature configured to mate with the first sensor; and a fourth alignment feature configured to mate with a second sensor.

18. The catheter system of claim 17, further comprising a port formed in the first support structure, the port connecting an exterior surface of the first support structure to an interior surface of the first alignment feature.

19. The catheter system of claim 17, wherein the first support structure comprises a first set of steering wire passageways, including the second alignment feature, and the second support structure comprises a second set of steering wire passageways, at least one steering wire, including the navigation control device, extending through the second set of steering wire passageways and into the first set of steering wire passageways.

20. The catheter system of claim 17, wherein the first support structure is such that a proximal surface of the first support structure is coupled to a distal surface of the distal portion of the elongate flexible catheter.

\* \* \* \* \*

UNITED STATES PATENT AND TRADEMARK OFFICE
CERTIFICATE OF CORRECTION

PATENT NO. : 12,390,123 B2
APPLICATION NO. : 17/894515
DATED : August 19, 2025
INVENTOR(S) : Anoop B. Kowshik et al.

Page 1 of 1

It is certified that error appears in the above-identified patent and that said Letters Patent is hereby corrected as shown below:

In the Specification

Column 2, Line 46, change "amity" to -- clarity --

Column 4, Line 15, change "steeling" to -- steering --

Column 4, Line 39, change "(Mill)" to -- (MRI) --

Column 9, Line 34, change "steeling" to -- steering --

Signed and Sealed this
Sixteenth Day of September, 2025

Coke Morgan Stewart
*Acting Director of the United States Patent and Trademark Office*